(12) United States Patent
Oravecz et al.

(10) Patent No.: US 7,000,475 B2
(45) Date of Patent: Feb. 21, 2006

(54) ACOUSTIC MICRO IMAGING METHOD AND APPARATUS FOR CAPTURING 4D ACOUSTIC REFLECTION VIRTUAL SAMPLES

(75) Inventors: Michael G. Oravecz, Naperville, IL (US); Alan Basterfield, Hazelbury Bryan (GB)

(73) Assignee: Sonoscan, Inc., Elk Grove Village, IL (US)

( * ) Notice: Subject to any disclaimer, the term of this patent is extended or adjusted under 35 U.S.C. 154(b) by 0 days.

(21) Appl. No.: 11/090,965

(22) Filed: Mar. 25, 2005

(65) Prior Publication Data

US 2005/0229707 A1 Oct. 20, 2005

Related U.S. Application Data

(63) Continuation of application No. 09/911,602, filed on Jul. 24, 2001, now Pat. No. 6,895,820.

(51) Int. Cl.
*G01N 29/06* (2006.01)
(52) U.S. Cl. .......................................... 73/602; 73/627
(58) Field of Classification Search ................ 73/602, 73/627, 629
See application file for complete search history.

(56) References Cited

U.S. PATENT DOCUMENTS

| | | | |
|---|---|---|---|
| 4,043,181 A | 8/1977 | Nigam | |
| 4,241,608 A * | 12/1980 | Dees et al. ................... | 73/606 |
| 4,387,597 A * | 6/1983 | Brandestini .................. | 73/626 |
| 4,566,459 A * | 1/1986 | Umemura et al. .......... | 600/443 |
| 4,733,562 A * | 3/1988 | Saugeon ...................... | 73/626 |
| 4,980,865 A | 12/1990 | Ishibashi et al. | |
| 5,078,145 A | 1/1992 | Furuhata | |
| 5,396,890 A | 3/1995 | Weng | |
| 5,515,856 A | 5/1996 | Olstad et al. | |
| 5,546,807 A * | 8/1996 | Oxaal et al. .................. | 73/606 |
| 5,897,499 A | 4/1999 | Machida | |
| 6,200,266 B1 | 3/2001 | Shokrollahi | |
| 6,374,675 B1 | 4/2002 | DePetrillo | |
| 6,500,118 B1 | 12/2002 | Hashimoto | |
| 6,895,820 B1 * | 5/2005 | Oravecz et al. ............... | 73/602 |

FOREIGN PATENT DOCUMENTS

| | | |
|---|---|---|
| JP | 10277042 A | 10/1998 |
| JP | 11009604 A | 1/1999 |
| JP | 2001-132664 A | 5/2000 |

OTHER PUBLICATIONS

Survey Sheds Light on Irksome Die Cracks, Tom Adams; 1 Page (doublesided); Reprinted from the Aug. 1996 edition of Solid State Technology—Copyright 1996 by Pennwell Publishing Company.

Brouchure of Sonoscan, Inc., Sonomicroscope System 3100 C-Mode Scanning Acoustic Microscope (C-SAM); six (6) pages; Copyright 1988 Sonoscan, Inc.

* cited by examiner

*Primary Examiner*—Hezron Williams
*Assistant Examiner*—Rose M. Miller
(74) *Attorney, Agent, or Firm*—Welsh & Katz, Ltd.

(57) ABSTRACT

For use in acoustic micro imaging, a method (and implementing apparatus) is disclosed for creating a 4D virtual sample data memory. The method comprises employing a pulsed ultrasonic microscope probe to interrogate a sample at three-dimensionally varied locations in the sample. Data developed by the microscope probe includes for each location interrogated a digitized A-scan for that location. The developed data is stored in a data memory.

9 Claims, 10 Drawing Sheets

GENERAL SAMPLE

ACOUSTIC MICRO IMAGING METHOD AND APPARATUS FOR CAPTURING 4D ACOUSTIC REFLECTION VIRTUAL SAMPLES

This application is a continuation of Ser. No. 09/911,602 filed Jul. 24, 2001, now U.S. Pat. No. 6,895,820.

RELATED APPLICATIONS

This application is related to, but not dependent upon, application Ser. No. 09/911,602, filed Jul. 24, 2001 for Acoustic Micro Imaging Method and Apparatus for Capturing 4D Acoustic Reflection Virtual Samples, and application Ser. No. 10/007,984, filed Nov. 13, 2001 for Frequency Domain Processing of Scanning Acoustic Micro Imaging Signals, both assigned to the assignee of the present invention.

BACKGROUND OF THE INVENTION

This invention concerns improvements in the field of non-destructive testing and failure analysis using pulsed ultrasound as a material probe. While many of the applications of the invention are useful in a broad range of applications, the invention will be described in the context of acoustic micro imaging ("AMI"). To further an understanding of the broad applicability of the principles of the invention, a brief description will be engaged of various scanning modes commonly employed today in AMI.

Figure 1:
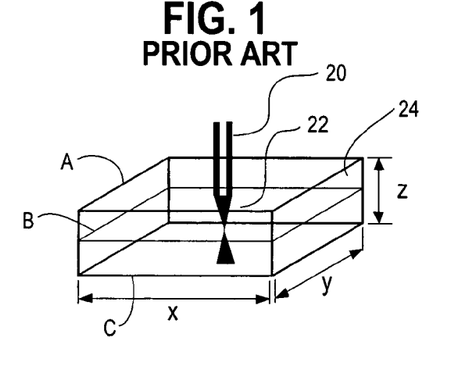
FIGS. 1–13 and 15 illustrate in highly schematic fashion various prior art AMI scanning modes.
Figure 1A:
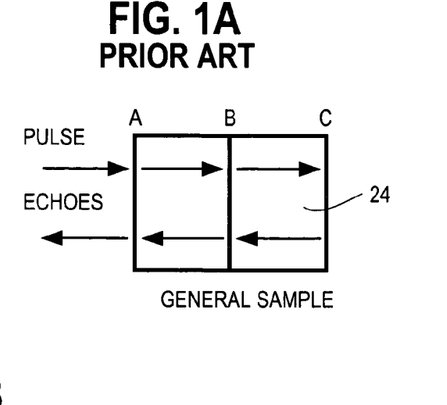
FIGS. 1A, 1B, 2A and 14 are illustrations useful in understanding general AMI principles.

The most basic form of acoustic interrogation is illustrated in FIG. 1 in which an ultrasonic transducer 20 is excited with a sharp electrical pulse and emits a pulse of ultrasonic energy which is brought to a focus 22 within sample 24 by a lens (not shown) at the distal end of the transducer 20. FIG. 1A is intended to represent the sample 24 as having a front surface A, an internal interface (acoustic impedance mismatch), and a bottom surface C. An acoustic (sometimes termed herein "ultrasound") pulse is reflected from the front surface A, interior interface B and bottom surface C and sensed by the transducer 20.

Figure 1B:
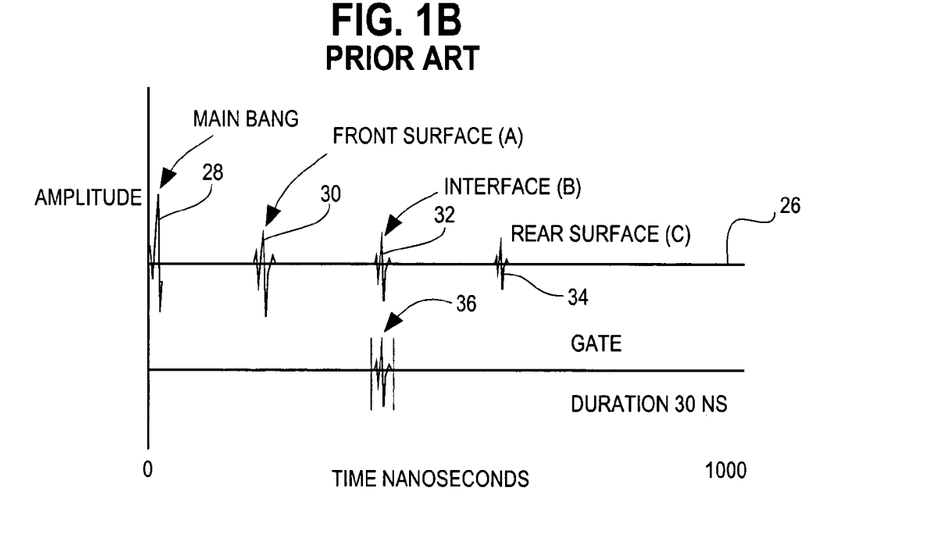

The amplitude of the reflected acoustic waveform as a function of time is shown in highly simplistic form FIG. 1B. The waveform 26 is commonly known as the "A" waveform or "A-scan", and in practice contains a great deal of information about acoustic impedance perturbations or features in the body of the sample.

In waveform 26 the first spike 28 is the "main bang" resulting from the electrical excitation of the transducer 20. A second spike 30 occurs later in time and is the sensed reflection from front surface A of the sample body 24. Still later in time, the transducer senses a reflection 32 from the interface B, and finally a reflection 34 from the rear surface C of the sample body 24.

As will be described in more detail below, acoustic microscopes employ a time window or "gate" 36 which passes only returned reflections which lie within a certain span of time corresponding to a certain depth in the sample. In FIG. 1B gate 36 is set to pass only the signal representing interface B reflection 32.

Figure 2:
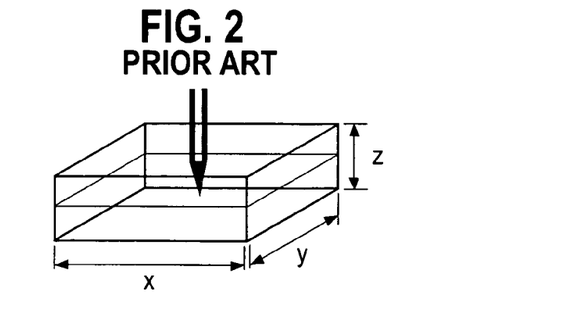
Figure 2A:
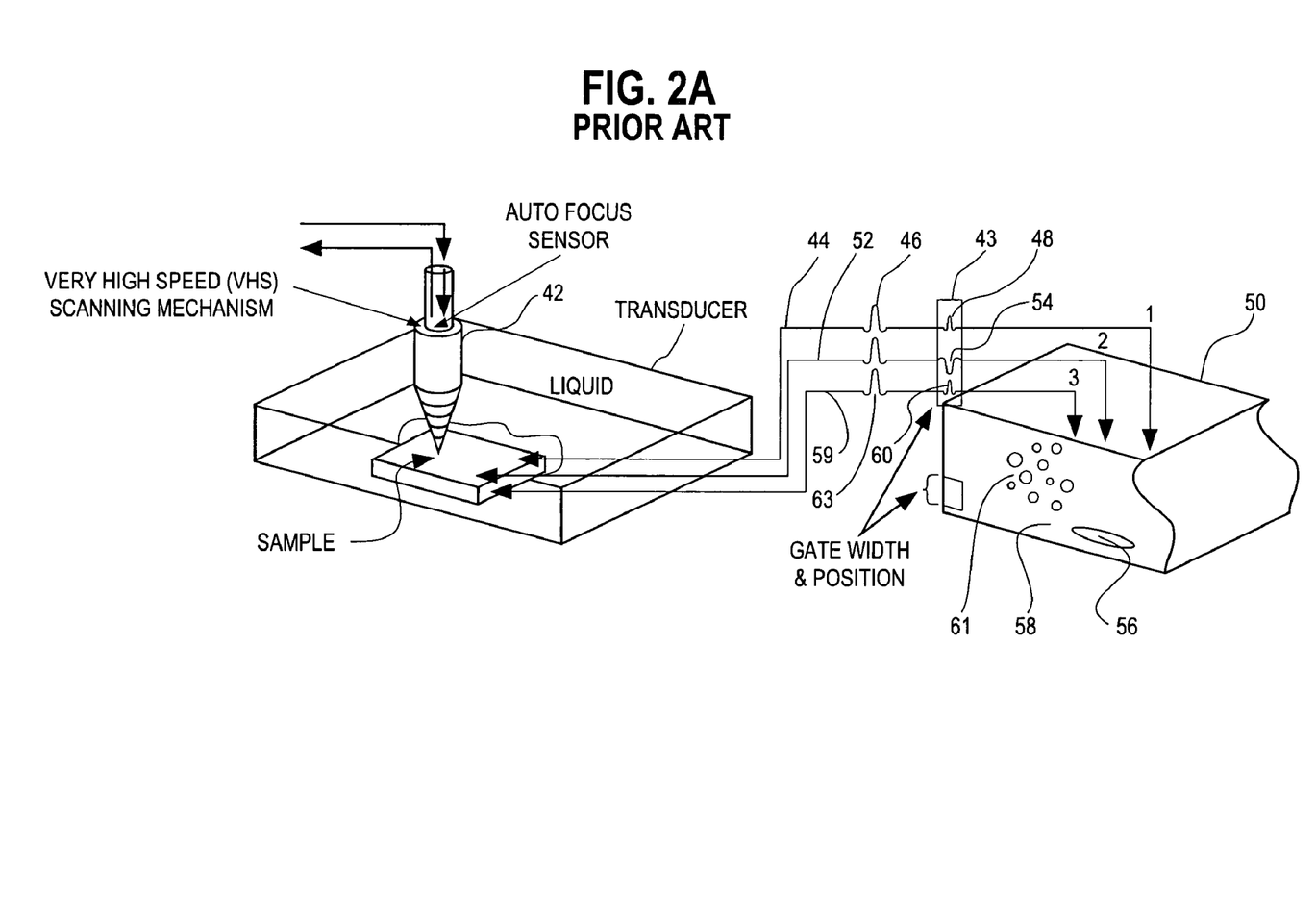

FIG. 2 represents in highly schematic form the "C-Mode" scan wherein a focused image is formed of an X-Y plane at a specific depth in the Z axis. FIG. 2A is another illustration of a C-Mode scan, showing the A-scan waveform produced from an interrogation by transducer 42 of three different Points 1, 2, and 3 in the sample. At Point 1, the A waveform 44 shows a reflection 46 at the front surface and a smaller reflection from an interface 48 in the sample 50. A waveform 52 associated with X-Y Point 2 shows a reflection 54 from an air gap 56 formed in the interface 58. The reflection 54 shows a phase reversal because of the lower impedance of air than of the sample material. Waveform 59 associated with Point 3 reveals a small amplitude reflection 60 from what may be an occlusion 62 in the body of the sample 50. The polarity of the reflection 60, being the same as that of the first reflection 63, suggests that the reflection 60 is not from an air void or other feature having lower acoustic impedance than that of the sample material.

In C-Mode scanning, a gate is set, as shown at 43 in FIG. 2A, for example, within which a peak detector (not shown) detects the peak value of the gated signal segments. The peak values detected are stored in a 2D (spatial) X-Y memory (not shown).

In C-Mode scanning acoustic microscopy a focused spot of ultrasound is generated by an acoustic lens assembly at frequencies typically in the range of 10 MHz to 200 MHz or more. The ultrasound is conducted to the sample by a coupling medium, usually water or an inert fluid. The angle of the rays from the lens is generally kept small so that the incident ultrasound does not exceed the critical angle of refraction between the fluid coupling and the solid sample. The focal distance into the sample is shortened by the refraction at the interface between the fluid coupling and the solid sample.

The transducer alternately acts as sender and receiver, being electronically switched between transmit and receive modes. A very short acoustic pulse enters the sample, and return acoustic reflectances are produced at the sample surface and at specific impedance interfaces and other features within the sample. The return times are a function of the distance from the encountered impedance feature to the transducer and the velocity of sound in the sample material(s).

An oscilloscope display of the acoustic reflectance pattern (the A scan) will clearly show the depth levels of impedance features and their respective time-distance relationships from the sample surface.

This provides a basis for investigating anomalies at specific levels within a part. The gated acoustic reflectance amplitude is used to modulate a CRT that is one-to-one correlated with the transducer position to display reflectance information at a specific level in the sample corresponding to the position of the chosen gate in time.

With regard to the depth zone within a sample that is accessible by C-scan techniques, it is well known that the large acoustic reflectance from a liquid/solid interface (the top surface of the sample) masks the small acoustic reflectances that may occur near the surface within the solid material. This characteristic is known as the dead zone, and its size is usually of the order of a few wavelengths of sound.

Far below the surface, the maximum depth of penetration is determined by a number of factors, including the attenuation losses in the sample and the geometric refraction of the acoustic rays which shorten the lens focus in the solid material. Therefore, depending upon the depth of interest within a sample, a proper transducer and lens must be used for optimum results.

In C-Mode scanning acoustic microscopy ("C-SAM"), contrast changes compared to the background constitute the important information. Voids, cracks, disbonds, and other impedance features provide high contrast and are easily distinguished from the background. Combined with the ability to gate and focus at specific levels, C-SAM is a powerful tool for analyzing the nature of any acoustic impedance feature within a sample.

In this type of C-mode scanning, the A-scan for each point interrogated by the ultrasonic probe is discarded except for the image value(s) desired for that pixel. Two examples of image value data are: (a) the peak detected amplitude and polarity, or (b) the time interval from the sample's surface echo to an internal echo (the so-called "time-of-flight" of "TOF" data).

Figure 3:
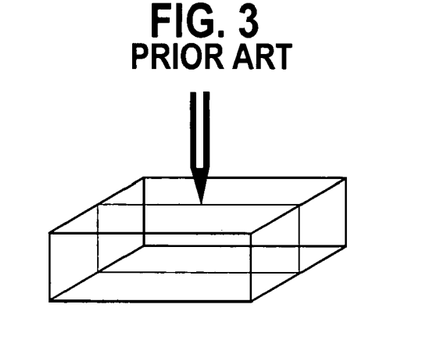

FIG. 3 illustrates the "B-Scan" mode which produces nondestructive cross-section data displayed as amplitude values of digital samples of A-Scan waveforms arrayed in a simulated X-Z plane of the sample.

Figure 4:
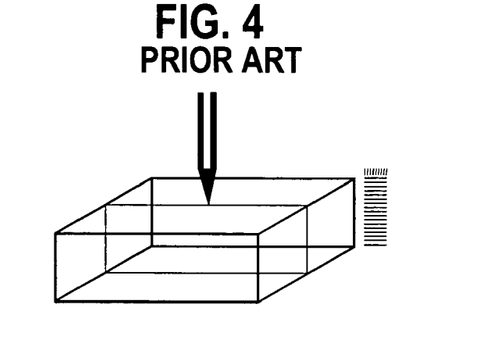

FIG. 4 is another mode related to the B-Scan mode and is termed by the assignee of this invention as the Quantitative B-Scan Analysis Mode, or "Q-BAM". A Q-BAM scan produces a calibrated, nondestructive cross-section of data in the X-Z plane of the sample. The data captured is caused to be completely in focus through the entire Z depth by scanning at various Z positions and readjusting the transducer focus before each successive scan. The position of the probe focus and the gate are automatically linked such that the gated segment of the waveform always represents reflections from impedance features which are in focus.

Figure 5:
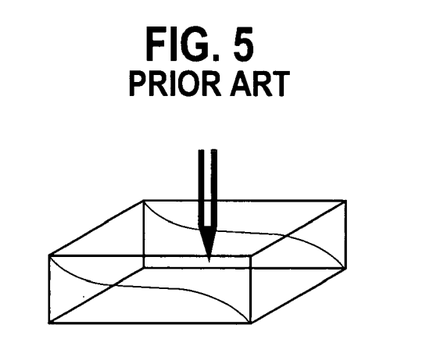

FIG. 5 illustrates a scan mode known as Three Dimensional Time-of-Flight or "3D TOF" which internally tracks first interface topography within a sample. Color-coded 3D graphic imagery is commonly employed to show the TOF topography of the inspected feature in relation to its distance from the top surface of the inspected sample.

Figure 6:
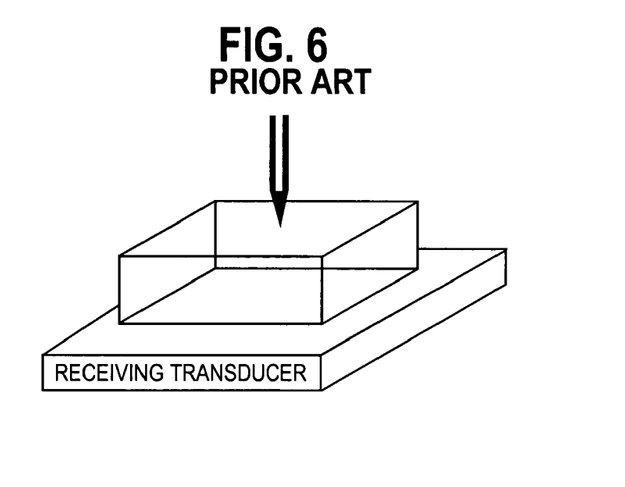

FIG. 6 shows a transmission mode which investigates the entire thickness of the sample in one scan. It is the ideal scan mode for rapidly identifying gross anomalies such as a die disbond. The anomaly detected can later be isolated and inspected in detail with C-Mode analysis.

Figure 7:
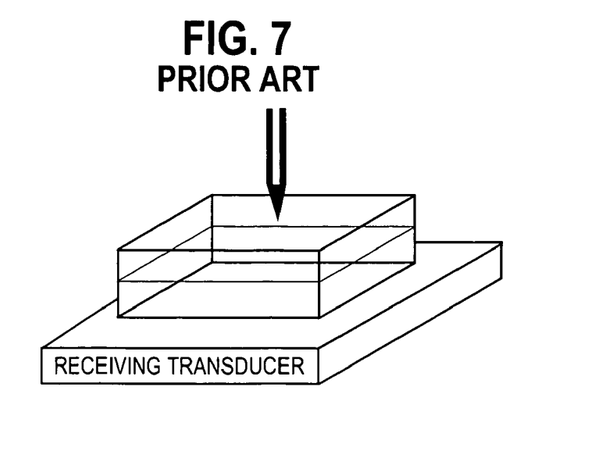

FIG. 7 represents a combination of reflection and transmission mode scanning. In one X-Y scan the entire thickness and a specific interface or anomaly can be inspected.

Figure 8:
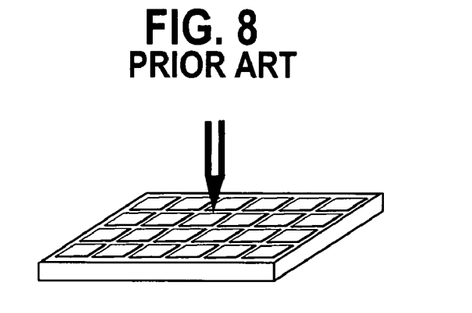
Figure 9:
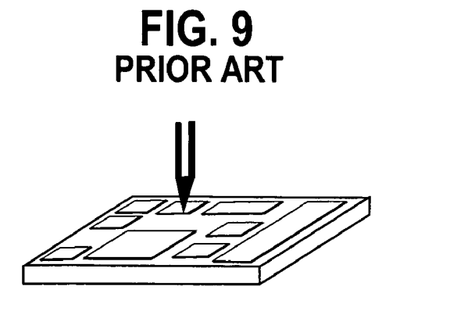

As represented schematically in FIG. 8, AMI is commonly employed to automatically position, focus, scan, analyze and report on acoustically detectable features in a tray of parts such as integrated circuits. FIG. 9 shows a similar application for ultrasonically inspecting various parts or locations on a PC board. The process is designed to automatically examine multiple types of parts located at specific locations on the PC board.

Figure 10:
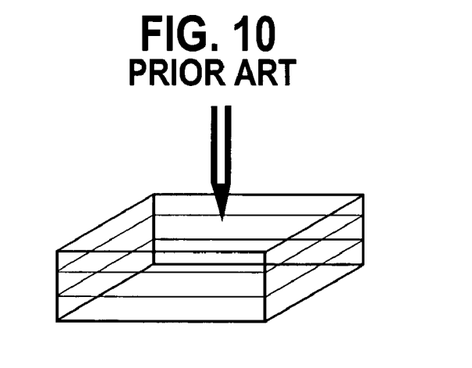

FIG. 10 depicts a "bulk-scan" mode which provides two dimensional (X,Y) display and measurement of material properties throughout a predetermined gated thickness (Z depth) in the examined part.

Figure 11:
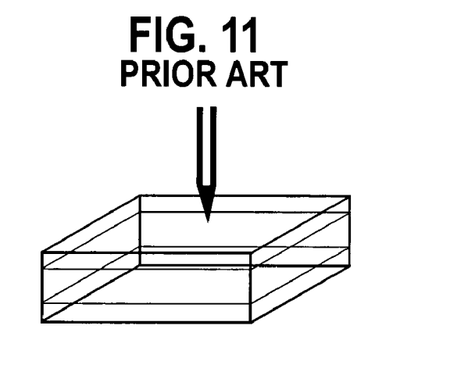

Multi-Scan (FIG. 11) is a way to obtain multiple C-Mode images with one scan at preseleted interfaces, or obtain a C-Mode and Bulk-Scan image simultaneously. It is ideally suited for applications such as simultaneous overmold material and interface bond analysis.

Figure 12:
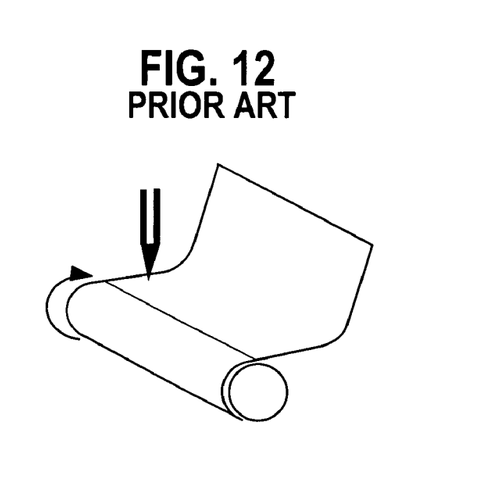

FIG. 12 illustrates an "R-Scan" mode—a rotational scanner which locates hidden defects within the circumference of a cylindrical sample. Nondestructively it "unwraps" and displays two dimensional (X,theta) image from 0 to 360 degrees of rotation.

Figure 13:
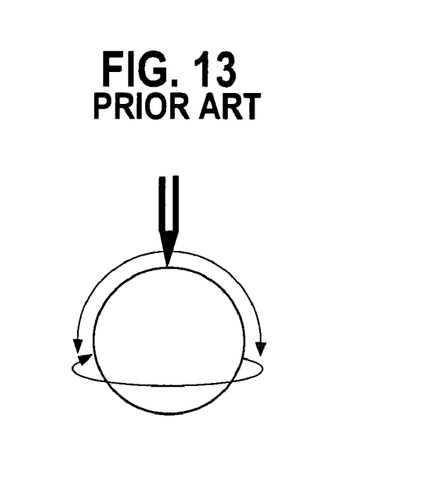

FIG. 13 is a mode for scanning spherical surfaces and subsurfaces. Hidden defects and flaws are first located and then C-Mode imaged for confirmation.

Figure 14:
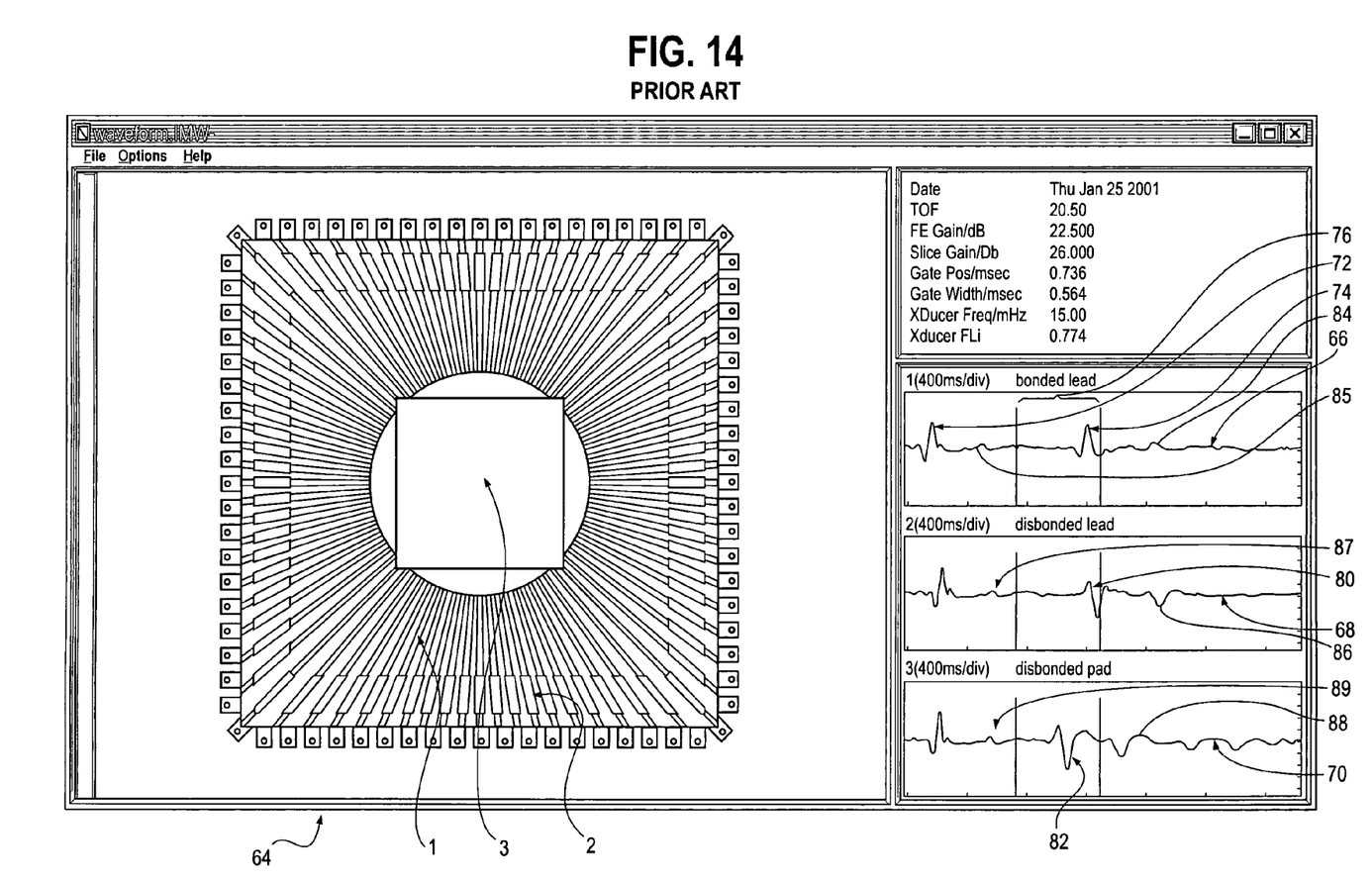

FIG. 14 a screen print of a monitor image formed using a commercial C-Mode scanning acoustic microscope manufactured by the assignee of the present invention. The sample was an encapsulated integrated circuit having a die attached to a pad, with leads extending radially from all sides of the die.

As noted, the "time of flight" of the acoustic pulses from transducer to sample front surface was 20. 50 microseconds. The front end ("FE") gain was set at 22. 500 dB, and the slice gain at 26. 000 dB. The gate was positioned at 0. 736 microseconds from the front surface echo and had a width of 0. 564 microseconds in order to capture a depth in the package embracing the die leads and the die-pad interface. The transducer frequency was 15 MHz and the transducer focal length was 0. 774 inch.

Acoustic reflectance signals 66, 68, 70 were stimulated by the transducer at three location, numbered "1", "2", and "3", respectively. Location "1" was on a bonded lead. The white color in the image reproduction signifies a sound bond between the inspected lead and the encapsulating material. Corresponding acoustic reflectance signal 66 shows a reflection 72 from the front surface of the package. Less than 1 microsecond later, we see a positive polarity reflection 74 from the soundly bonded lead. As the reflection 74 is within the reproduction gate 76, the reflection 74 is rendered in the image 64.

However, with the probe at position "2" over a different lead, we see in acoustic reflectance signal 68 a negative polarity reflection 80, indicating that the acoustic wave encountered an interface with a lower acoustic impedance than that of the sample material. The logical interpretation of this data is that the lead at position "2" is disbanded and that the resulting air gap is responsible for the phase reversal of the reflection 80. Again, because the reflection 80 is within the gate, it is visualized in the image 64.

With the probe at position "3" on the die-pad interface, acoustic reflectance signal 70 shows a negative polarity reflection from the interface, indicating a die-pad disbond (air gap). The location of the reflection 82 closer to the front surface reflection 72 indicates that the die-pad interface is slightly higher (closer to the probe) than the leads at positions "1" and "2".

As described above, in conventional C-Mode AMI, the only data that is captured and stored for display and analysis is the peak value of the amplitude waveform within the gate 76, optionally along with polarity and TOF data. All other data are lost. Note in each of the three acoustic reflectance signals 66, 68, 70, the acoustic impedance perturbations appearing as ripples 84, 86, 88 at depths below the gate 76. Also, the ripples 85, 87, 89 occurring above the gate 76,78. Using conventional C-Mode AMI, the potentially valuable information contained in those ripples is lost forever.

Thus, from the above description it is well known in the field of acoustic image microscopy to capture an X-Y set of data points, each point representing the detected peak of a gated region of an amplitude-modulated acoustic signal reflected from impedance features within the body of an insonified solid part. The set of data points may be visualized, for example on the screen of a computer monitor.

By moving the position of the gate along the time axis of the acoustic reflectance signal, a particular plane or layer within the examined part may be inspected. To increase the resolution capability of the X-Y dataset at varying depths through the solid, it is known to coincide the focus of the acoustic transducer employed with the gated region of the part.

Figure 15:
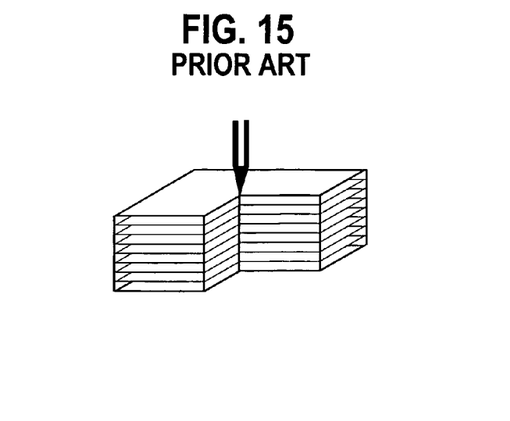

Referring to FIG. 15, this process "slices" the part into as many horizontal sections as desired. Typically 10 slices are adequate for thin samples such as integrated circuits, however, up to 200 slices can be made on commercially available AMI equipment. Equipment software can be set to divide the part into equal thickness slices. Each slice is then automatically scanned with the focus and gate optimized for each specific slice depth. As in C-Mode scanning, the reflectance signals are gated and peak amplitude values are stored. After scanning, the slices may be displayed simultaneously as "thumbnail" images on a computer monitor screen. Typically the slices are reviewed in detail or thumbnail images are reviewed in a slide show sequence—a process analogous to descending acoustically through the part or peeling it apart layer by layer.

The described equipment has software which assembles the slices and reconstructs the data into an "acoustic solid". The acoustic solid can be rotated to any desired angle of view. With this software, an operator can also visualize cross-sections of the acoustic solid. Sectioning can take many different forms—a single horizontal, vertical or diagonal section can be removed. Multiple sections or "bits" can be removed which are defined by material properties, rather than by geometry. For example, an operator might remove all of the molding compound from an IC package and still leave intact the image of a crack within the molding compound.

As described, the acoustic solids created by effectively stacking an array of such X-Y data sets have proven to be useful in certain applications where the information desired to be recorded and displayed is simply the signal peaks in the gated regions of interest. However, many applications exist wherein the information desired to be retrieved from the solid part is not precisely known at the time the part is acoustically interrogated. Since the acoustic reflectance signals returned from each pulse are lost, except for the peak of the signal within the gated region (and optionally, polarity and TOF data), it is not possible to derive additional information from the stored X-Y-Z data set of amplitude peak values. It is not possible off-line, for example, to adjust the position of the gate to change the depth of the inspected plane. Nor is it possible to employ signal processing analytics on the missing acoustic signal information to learn more about the anomalies which perturbed the insonifying sound pulses.

Another prior art approach employed in AMI differs from the above description in at least respect. One X-Y scan across a sample is employed with a transducer having a high F-number lens. The acoustic reflectance signal (A-scan) is captured, digitized, and stored as digital data. Because the capture gate may be as wide as the specimen (or the zone of interest) is deep, reflections from all levels in the specimen are stored. After capture of the ungated, full volume waveform, a gate (or multiple gates) can be introduced at any position to visualize reflecting features in a specimen at a depth and thickness corresponding to the gate location and width.

In this approach, the acoustic waveform for each pixel is saved to storage means (memory, hard drive, etc.). The number of samples in a stored waveform may vary depending on the application and any implementation specific limits. For example, 1 to 4 microseconds of the acoustic waveform, including and after the surface echo, may be stored. At a 1 GHz sampling rate, this would represent 1000 to 4000 samples per each pixel's acoustic waveform. The total number of pixels in an image depends on the chosen image resolution. Typical image resolutions include: 256. times. 240, 512. times. 480, and 1024. times. 960. The total storage required grows rapidly as the resolution increases.

The last-described scan mode provides the data for a 2-dimensional B-scan. Depending upon the transducer, either all or only a small part of the stored waveform may be within the focused region of the ultrasonic beam. Or, depending upon the transducer and the sample, either all or only a small part of the sample's thickness may be covered by the stored waveform. Or, depending upon the transducer and the sample, either all or only a small part of the sample's thickness may be within the focused region of the ultrasonic beam.

The advantage of this approach is that the full acoustic reflectance waveform is captured and digitized for later review, gating and processing. No information is irretrievably discarded as in conventional C-Scan approach which employs gated peak detection and storage of gated signal peaks (which become the image pixels upon display), and, optionally polarity and time-of-flight data. As described, to produce a display of any particular level or levels within the sample, the gating is set for that level or levels.

One obvious and significant disadvantage of this approach, however, is that all images generated by changing gate position are not in sharp focus. An attempt is made to place the entire specimen depth in focus which means that no plane is in the sharpest possible focus. As will become evident from the ensuing description, another drawback of moment of this last-described approach is the limited amount of data that can be gathered in a single scan of the sample.

OBJECTS OF THE INVENTION

It is a primary object of the present invention to provide apparatus and method for capturing space-time acoustic reflection data in an examined real sample in the form of a "virtual sample" volume or layer. The captured virtual sample contains, for each interrogated point in 3 or 2 spatial dimensions, data representing a time-varying acoustic reflection waveform.

It is another object that such captured virtual sample contain all the data which an operator could collect during the inspecting of a real sample, permitting the virtual sample to be re-examined off-line just as though the real sample were available.

Another significant object of the present invention is to capture dramatically greater data than in any prior method, making possible a more accurate and comprehensive understanding of the internal acoustic impedance structure within an examined sample.

It is still another object that in a preferred execution of the invention, detectable acoustic reflection features are captured in each of a plurality of stored A-scans.

It is yet another feature of a method according to this invention that reflection waveform amplitude errors are compensated such that displays modulated by such data exhibit accurate brightness levels throughout the image.

DESCRIPTION OF THE PREFERRED EMBODIMENTS

In a general sense as applied to AMI, the invention concerns an improved method and apparatus for capturing data characterizing acoustic impedance features in an examined plane or volume of a sample. The method may be beneficially employed in a scanning acoustic microscope having a pulsed ultrasonic probe and a probe translation stage for translating the probe in a sample, or a sample translation stage moving the sample relative to the probe.

Reviewing the various prior art scan modes illustrated in FIGS. 1–15 it will be understood that an A-scan (FIG. 1B, for example) can be thought of as representing reflection data in a time dimension for a single point in the sample examined—that is, reflection amplitude detected at the transducer as a function of time (time being associated with depth in the examined sample).

Throughout this application, reference is made to an A-scan representing reflection data in a time dimension for a single point in the sample examined, or similar language. It is important to understand that this descriptive nomenclature is used for convenience. In actuality an A-scan represents reflection data in a time dimension for a single set of ultrasonic excitation conditions or parameters. These conditions or parameters include the location in the sample of the transducer focal point (point of smallest cross-sectional area of the probe waist), sometimes termed herein the "transducer focal point", "focal point", "point", "transducer focus", "focus", or other similar language. The set of excitation conditions also includes the probe spot size, ultrasound frequency and bandwidth, pulse height (energy), and transducer depth of field.

However, of these excitation conditions, the only one that is typically varied during the practice of the present invention is the location of the transducer focal point. The remaining conditions are held constant. For that reason, for ease of explanation of the present invention, when the application speaks of an A-scan representing reflection data for a single point in the examined sample (or similar language), it is to be understood that what is meant is reflection data corresponding to a particular set of excitation conditions, including the location of a single transducer focal point in the examined sample.

A C-scan (FIGS. 2, 2A) results in a capture of peak values of gated reflection waveform segments associated with a collection of data points in an area—specifically the X-Y plane. A C-scan thus results in storage of reflection amplitude values in 2 spatial dimensions, but does not include time-varying (A-scan type) data. A Q-BAM scan (FIG. 4) is similar to a C-scan, again resulting in a capture of gated peak reflection values for points in an area specifically the X-Z plane, with no time (A-scan) data being stored. A series of C-scans may be employed (FIG. 15) to capture a 3D set of gated peak reflection values of points in a sample or sample region of interest, again with no time (A-scan) data being stored.

This invention provides a 4D (three spatial dimensions and one time dimension) data set which represents a true virtual sample—one which has all the information stored in memory that could be derived from the real sample, for a given transducer, pulse rate and other operating conditions. As will be explained in more detail below, the data is preferably gathered by repeated interrogations of the sample while varying the focus of the pulsed ultrasonic probe employed such that detectable reflectance features are captured in each of a plurality of stored A-scans. Assuming the transducer depth of field to be less than the sample depth, in certain of the A-scans the reflection features will be stored in in-focus data, and in others in out-of-focus reflection data.

As used in this application, "in-focus acoustic reflectance data" means reflectance data from in-focus impedance features—that is, impedance features which are within the depth of focus of the interrogating ultrasonic probe. "Out-of-focus acoustic reflectance data" means reflectance data from out-of-focus impedance features—that is, impedance features which are not within the depth of focus of the interrogating ultrasonic probe. As used in this application, unless otherwise indicated, "focus" means the location of the interrogating probe.

This 4D data set can be retrieved from memory and manipulated to produce displays of slices of data representing any plane of data: X-Y, X-Z, Y-Z or any diagonal Z plane, with all reproductions exhibiting reflection data form in-focus impedance features in the sample. Three-dimensional volumes may be rotated, dissected and manipulated in any way desired, with all imagery representing in-focus reflection data.

In this application, the direction of the ultrasonic probe shall be taken to be the Z direction or axis. Planes parallel to the Z axis would include the "X-Z" plane, the "Y-Z" plane, or any X-Y diagonal plane or other plane which is parallel to the Z axis, that is, any plane which is not angled with respect to the Z axis. For convenience only, and not by way of limitation, in this specification and the appended claims, the "X-Z" plane shall mean all such planes parallel to the Z axis.

In the 3D (spatial dimensions) mode, the invention may be employed to capture space-time data throughout a sample volume or region of interest ("ROI") within a sample volume in any manner or geometry, independent of the scan mode or coordinate system (Cartesian, cylindrical, spherical, etc.).

Figure 16:
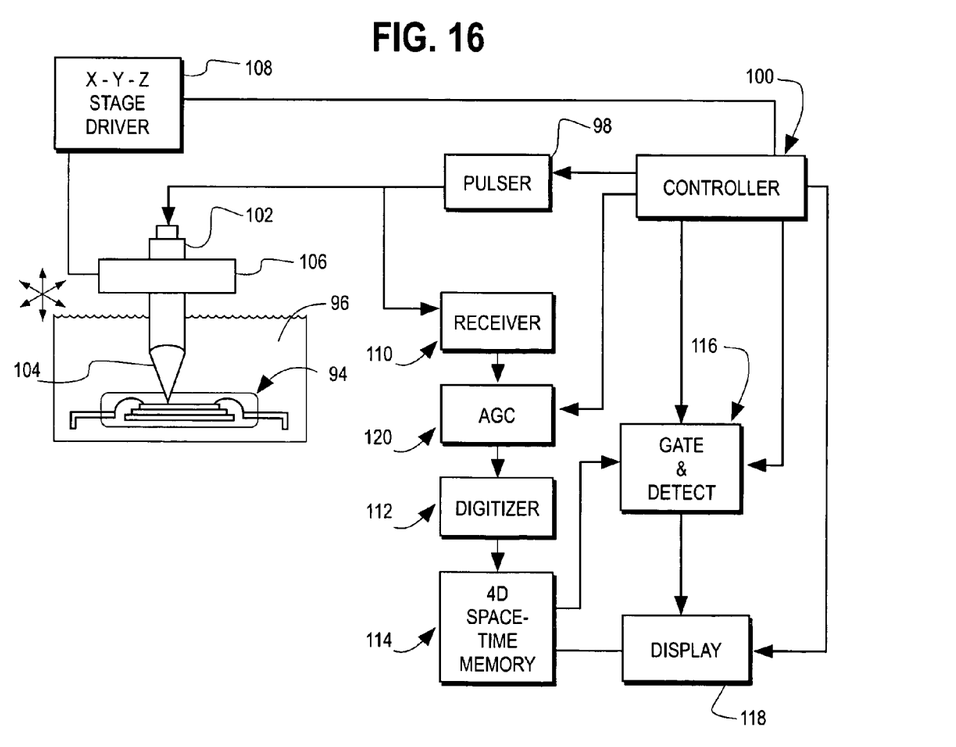
FIG. 16 is a schematic illustration of a preferred form of an acoustic imaging microscope which used to practice the teachings of the present invention.

FIG. 16 illustrates in highly schematic form an acoustic imaging microscope implementing the principles of the invention, shown as being adapted to inspect an integrated circuit ("IC") package 94 submerged in a coupling medium 96. Pulser 98, under the control of controller 100 excites a transducer 102 to generate a pulsed ultrasonic probe 104, typically at frequencies ranging from 10 MHz or lower to 230 MHz or higher. The transducer 102 is scanned in X, Y, and Z coordinates by an X-Y-Z stage 106 through an X-Y-Z stage driver 108 under the control of controller 100.

Acoustic reflections from impedance features in the IC package 96 are sensed by a receiver 1 10. Acoustic reflectance signals developed by receiver 1 10 are analog and take the form of acoustic reflectance signals 66, 68, or 70 in FIG. 14, for example. The analog acoustic reflectance signals developed by receiver 110 are supplied to an automatic or computer-driven gain control circuit ("AGC") 120. The AGC 120 is preferably employed to adjust the retrieved acoustic reflectance signal to correct or reduce signal amplitude errors such as may be caused by acoustic energy attenuation by the examined sample. The output of the AGC 120 is supplied to a digitizer 112 where the analog signals are quantized, for example by a 2 GS/s analog-to-digital converter, into digital bytes for storage in a 4D space-time memory 114.

The 4D space-time memory 114 is of a type adapted to store time-space data corresponding to three spatial dimensions, and associated with each point in 3D space, a set or sets of data corresponding to a variation or variations in one or more parameters associated with each point in space. In accordance with the present invention, for each point in a 3D volume, a sequence of data bytes are stored. The data bytes describe the time-dependent amplitude fluctuations of an acoustic reflectance signal returned from a particular point in sample space. The length of the stored acoustic reflectance signal is a function of the width of a capture gate that is set by the operator or generated by a program or algorithm.

As will become evident from a more detailed description to follow, to create a display the stored space-time data stored within memory 114 is, in one method, gated and peak detected in a gate and detect component 1 16 which may be a software algorithm or hardware signal processor. A conventional peak-detected output signal from component 116 is employed to modulate a display 120, which may be CRT monitor, for example. Alternatively, as is well known, time-of-flight data may also be displayed. In software, or in a hardware digital signal processor for speed, the system processes the 4000 digital values (in our example). The digital processing appropriately gates and peak detects the 4000 values to obtain the pixel value that will be displayed.

Figure 16A:
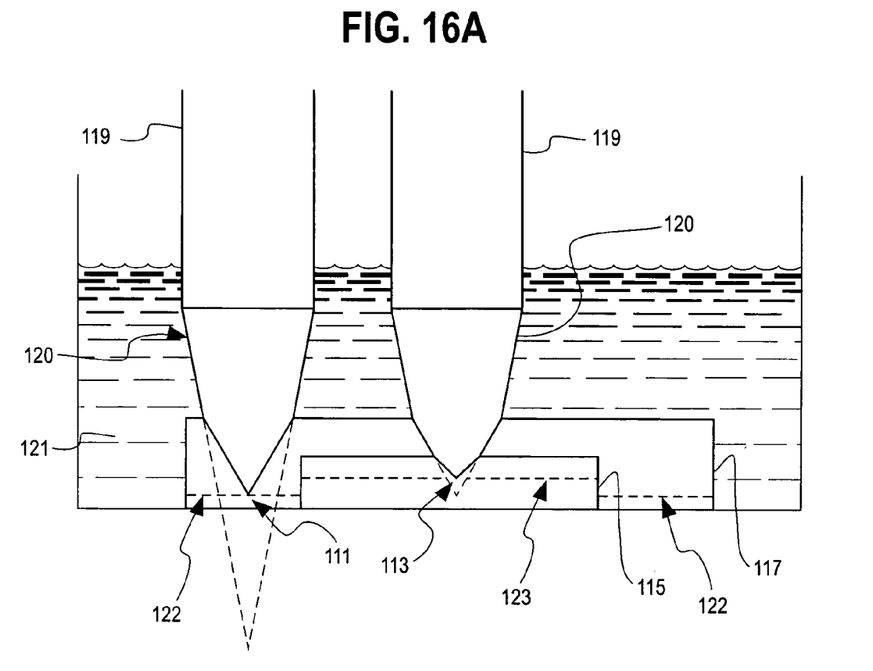

It is of note that in AMI discussions it is customary to speak or write of "scan planes" or "slices", when in fact a scan may not develop a true plane of interrogated points. FIG. 16A illustrates in highly schematic fashion the manner in which, in practice, a scanned plane can, for example, have an offset. An IC package is shown simplified as comprising a silicon die 115 encapsulated by an IC epoxy encapsulant 117. A transducer 119 emits an ultrasonic probe 120 transmitted to the IC package through a couplant such as a body 121 of water. As the acoustic index of epoxy is greater than that of water, the probe focus 111 is displaced toward the transducer 119 and scans a plane 122 within the epoxy encapsulant 117. As the transducer is translated into the region of the die 115, however, the probe focus 113 is displaced closer to the transducer 119 and scans a plane 123 offset from plane 122. For convenience it is common parlance to simply refer to a scan plane. That convention has been followed in this application.

It is a stated object of this invention to provide means and method for capturing 4D space-time acoustic reflection data in an examined real sample in the form of a "virtual sample" volume or layer. As explained, the virtual sample contains all the data, and permits all the displays, which an operator could have collected during real time examination of live sample. Thus, by this invention, the 4D virtual sample data can be manipulated off-line just as though the live sample were present. Further, as noted, detectable reflectance features are captured in each of a plurality of stored A-scans. Thus, assuming a shallow depth of field of the interrogating transducer compared to the capture-gated sample depth, the stored reflectance data will represent both in-focus acoustic reflectance data and out-of-focus acoustic reflectance data. The reconstructed displays are thus capable of exhibiting in-focus impedance features, out-of-focus impedance features, or combinations of both, or the results of inter-processing data representing both in-focus and out-of-focus impedance features. This capability is not possible with conventional C-Mode scanning acoustic microscopes which capture only peak values of gated signal segments, and discard the remaining information in the A-scan reflection signal from each interrogated x,y,z point within the sample.

Nor is this capability available with a system that makes one X-Y scan across a sample and saves the A-scan waveforms, as the data captured will not represent reflections from in-focus acoustic impedance features throughout the sample volume. Further, systems of this latter type capture only one bulk A-scan reflection for each x,y point in the sample. Simply stated, if 256. times. 240. times. 50 data points are to be inspected (50 being the number of inspection points or levels in the Z dimension parallel to the ultrasonic probe), such a system interrogates only 256×240 points in a single X-Y scan. As it must capture all information in one scan, a compromise focus is employed using a high F number transducer lens with a long focal length and therefore large spot size (point spread function). Inevitably, this one-shot approach means that no impedance features are truly in sharp focus, and displays developed from such a dataset will reflect this compromise approach with less-than-optimum resolution.

Let us assume an example where for each of 256. times. 240 x,y points, 50 A-scans will be captured—one for each of the assumed 50 values of "z". If we assume a narrow transducer depth of field compared to the capture-gated depth of the sample or sample region of interest (as is the case in the preferred executions of the invention), only a fraction of the "z" value scans will recover reflectance information from in-focus impedance features. However, that data will permit high resolution image reconstructions, as the impedance features will truly be in sharp focus. Further, the remaining A-waveforms from remaining z-differentiated x,y points may also contain very valuable data. By processing the in-focus reflection data with out-of-focus reflection data, significant additional information about internal reflection features can be gleaned.

It is highly desired in the inspection of a sample such as an IC package to gather as much information as possible about any internal voids, disbonds, cracks, occlusions, interfaces and other acoustic impedance features. Acoustic reflections from internal impedance features carry a tremendous amount of information in the detected A-scan waveforms. Every undulation in the return waveform indicates an acoustic impedance mismatch of some character within the examined sample. There are many factors which can influence the amplitude of the A-scan signal associated with each interrogated point in a sample, including:

a) the location in the sample of the transducer focus;

b) the size of the impedance feature (which influences the percentage of the acoustic wave which is intercepted);

c) the shape of the feature (concave, flat, convex, irregular, e. g. ) which will influence the direction of wave reflection or refraction;

d) the scattering property of the feature (how rough or smooth the feature is relative to the acoustic wavelength);

e) the acoustic impedance of the feature;

f) the impedance mismatch between adjacent features;

g) the attenuation properties of the various materials through which the ultrasound probe and return signal passes;

h) the thickness of the sample materials encountered and the total depth of the sample;

i) the spot size (point spread function) and location of the ultrasonic probe;

j) acoustic energy conversion between acoustic wave types (compression, surface, shear);

k) reverberation between interfaces and other impedance features;

l) interference cancellation effects;

m) the frequency of the ultrasound employed (which dramatically impacts acoustic attenuation);

n) masking effects (anomalies close to interfaces may mask closely adjacent features, as described);

o) focus errors due to refraction;

p) the height or energy of the pulses which are employed to excite the transducer;

q) trailing shear wave effects;

r) sample edge effects;

s) depth of field of the transducer;
t) number of features encountered (each reduces acoustic energy);
u) noise (mechanical, electrical or thermal);
v) features in the unfocused part of the beam bundle;
w) transducer ringing;
x) shadowing; and
y) specimen material anisotropy.

It is obviously critical therefore that as much internal acoustic impedance data as possible be gathered from the sample, and that such data be stored for later signal processing, analysis, interpretation and display.

In a general sense a method of the present invention for use in acoustic micro imaging is directed to capturing 4D space-time acoustic reflectance data to create a virtual sample volume or spaced virtual sample layers which characterize impedance features in a sample volume interrogated with a pulsed ultrasonic probe. The method comprises, in one execution, employing a pulsed ultrasonic microscope probe to interrogate a sample at three-dimensionally varied locations in the sample. Data produced by the pulsed microscope probe are developed. The data include for each location interrogated a digitized A-scan for that location. Finally, the developed data are stored in a data memory. In another aspect the method involves: a) deriving and storing a digitized non-peak-detected time-varying reflection signal for each location in a series of locations in a first plane of the sample volume; and b) deriving and storing a digitized non-peak-detected acoustic signal for each location in a series of locations in a second plane of the sample volume, said second plane being displaced from said first plane. The planes may be adjacent or spaced. The first plane may be the X-Y plane, or alternatively it could be the X-Z plane, Y-Z plane, or another plane containing the Z axis.

The stored signals create a 4D virtual sample data store containing data representing for each point in an interrogated sample volume three spatial dimensions and a time variable. The time variable comprises a digitized time-varying waveform characterizing reflections from acoustic impedance features in the examined sample.

The preferred apparatus for capturing data in accordance with present invention is an XY-Z scanning acoustic microscope as illustrated in FIG. 16 and described above. In the context of data capture employing a scanning acoustic microscope having a pulsed ultrasonic probe as depicted in FIG. 16, the method of the present invention is directed to capturing 4D space-time virtual sample data characterizing acoustic impedance features in an examined volume of a sample interrogated with the pulsed ultrasonic probe. The method involves: a) scanning a first plane in the sample; b) storing a digitized, non-peak-detected, time-varying acoustic reflectance signal for each interrogated point in the plane; c) scanning a second plane in the sample; d) storing a digitized, non-peak-detected, time-varying acoustic reflectance signal for each interrogated point in the second plane; and e) repeating the scanning and storing operations to capture space-time data representing a virtual sample volume corresponding to the examined real sample volume or region of interest.

The method preferably includes controlling the focus of the probe during each scanning operation such that each of the interrogated planes are within the depth of field of the probe-developing transducer when scanned. The scans may be made of variably spaced planes concentrated, for example, in a particular region of interest ("ROI") in the sample predicted to contain impedance features desired to be examined thoroughly. Or, more often, the method will be employed to successively scan adjacent planes. The planes may be X-Y or X-Z planes, or other planes containing the Z axis. However, most commonly the successively scanned planes will be those displaced in the Z axis of the probe. In the latter case, the displacement of the scans ideally is caused to be substantially equal to the depth of field of the transducer.

Figure 17:
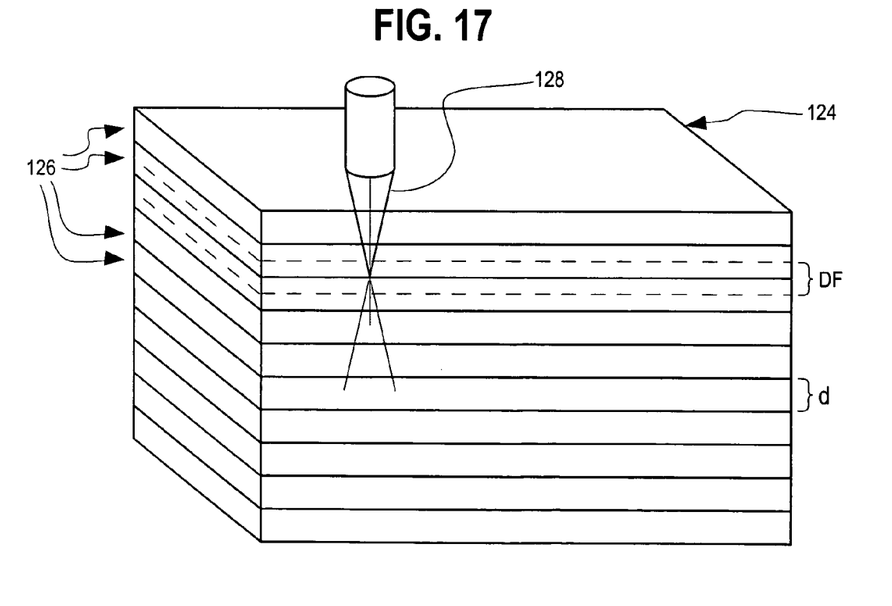
FIGS. 17–23 are schematic diagrams depicting various aspects of the present invention and its implementation.

FIG. 17 illustrates the last-described condition wherein a sample 124 is scanned in successive planes 126 displaced in the Z direction a distance "d" equal to the depth of field "DF" of the transducer 128. In this condition reflectance features are captured in stored in-focus acoustic reflectance data, and in stored out-of-focus acoustic reflectance data. As explained, all impedance features will be captured in reflection data from an "in focus" condition, that is, a condition wherein the features are within the depth of field of the transducer employed to generate the ultrasonic probe.

Figure 18:
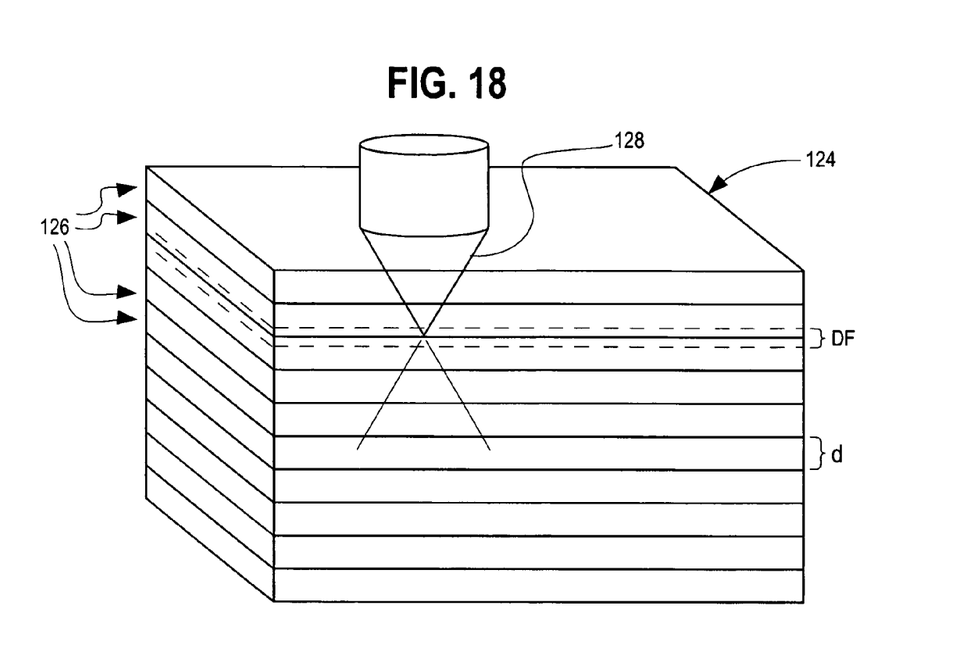

In certain applications or parts of the sample where data reduction is deemed more important than data density and display fidelity, the scans may be made in successive planes displaced in the direction of the probe by a distance which is greater than the depth of field of the transducer, creating an underscan condition. This condition is illustrated in FIG. 18 wherein like reference numerals have like meaning to those in FIG. 17.

Figure 19:
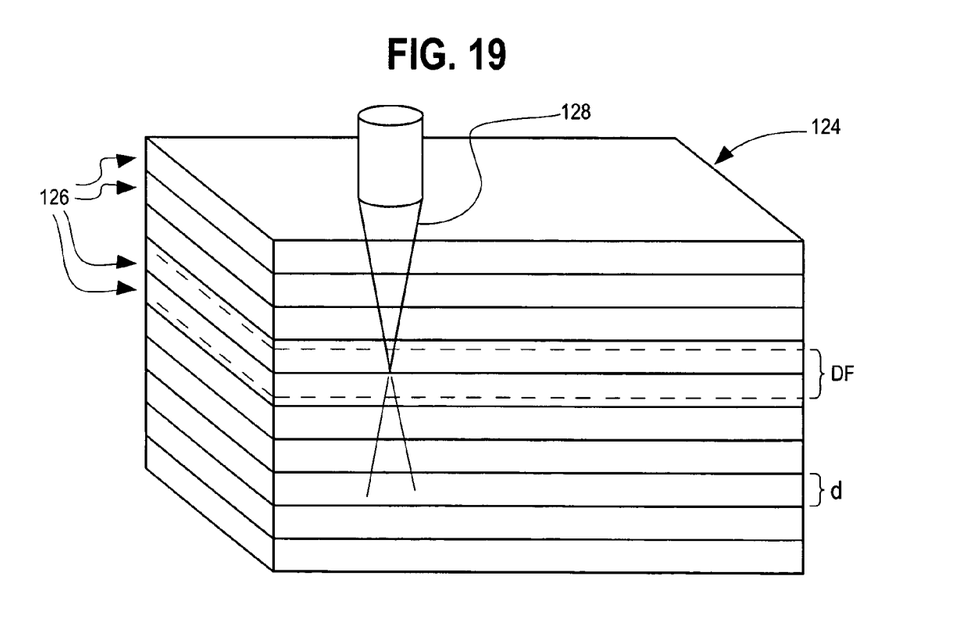

And finally, in applications where maximum information capture is of greater concern than data capture speed or data storage requirements, the scans may be made in adjacent planes displaced in the direction of the probe by a distance "d" which is less than the depth of field of the transducer 128, creating an overscan condition. See FIG. 19 wherein reference numerals have like meaning to those in FIGS. 17 and 18.

Figure 20:
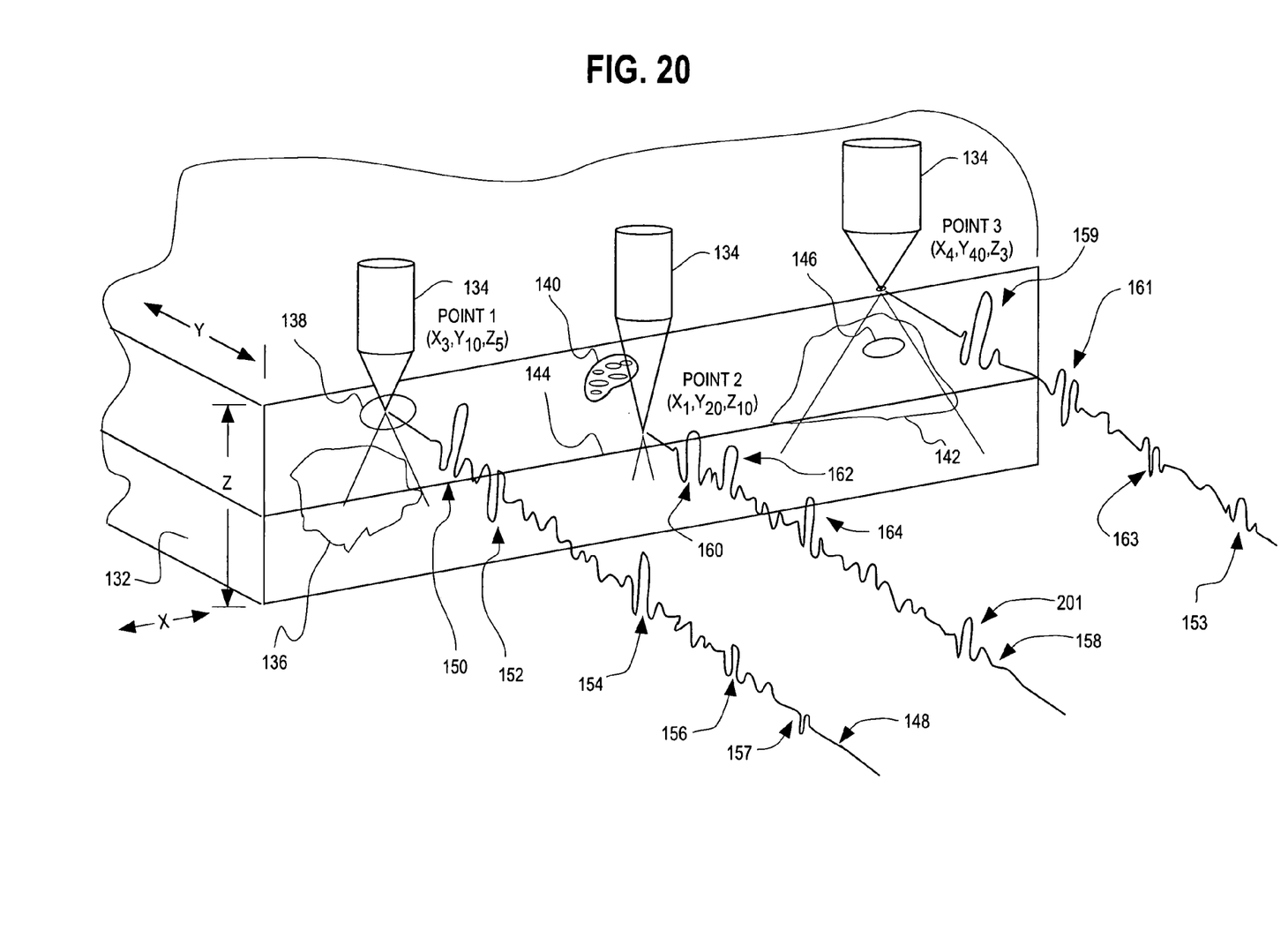

FIG. 20 illustrates a sample 132 which has been interrogated by an X-Y-Z raster scan or other scan mode to capture 4D space-time data in accordance with the present invention. For simplicity of description, FIG. 20 shows hypothetical A-scan waveforms developed from ultrasonic probe interrogations at three locations within the sample designated (x3,y10,z5), (x1,y20,z10) and (x4,y40,z3), hereinafter termed points 1, 2, and 3, respectively. The sample is shown as having impedance features in the forms of a crack 136, a large air bubble 138, a large occlusion 140, a disbond (air gap) 142 at an interface 144, and a small air bubble 146.

The acoustic reflectance signal (A-scan) 148 from point 1 exhibits a strong front surface reflection 150, a strong inverted phase reflection 152 from air bubble 138, a positive reflection 154 from interface 144, a weak positive reflection 156 from crack 136, and a very weak inverted phase reflection 157 from the back surface of the sample.

The A-scan 158 from Point 2 exhibits a positive front surface reflection 160, a strong closely adjacent positive reflection 162 from occlusion 140, a strong positive reflection 164 from the interface 144, and a weak reflection 201 from the back surface of the sample.

In practice, the reflections 152 and 162 will likely be partially masked by the strong front surface reflections 150, 160.

A-scan 153 shows a strong reflection 159 from the sample front surface, a weak inverted phase reflection 161 from the small air bubble 146, and a strong reflection 163 of inverted phase from the disbond 142. The A-scan 153 exhibits no reflection from the back surface because of the total shadowing of the back surface by the disbond 142.

As shown in FIG. 20, in accordance with a preferred execution of this invention, the ultrasonic probe is focused at Points 1, 2, and 3 in order to assure that the impedance features at those locations will be captured in in-focus reflectance data, as defined herein.

As explained above, the data is preferably gathered by repeated interrogations of the sample while varying the focus of the pulsed ultrasonic probe employed such that detectable reflectance features are captured in each of a plurality of stored A-scans. Assuming the transducer depth of field to be less than the sample depth, in certain of the A-scans the reflection features will be stored in in-focus reflection data, and in others in out-of-focus data.

Referring to FIG. 20, if it were desired to display data at level z5, for example, retrieved from a 4D memory such as shown at 114 in FIG. 16, in A-scan 148 inverted reflection 152 from air bubble 138 would represent in-focus reflectance data, that is, data from an impedance feature (air bubble 138) that was within the depth of field of the transducer 134 when interrogated. However, reflections 154, 156, and 157 from interface 154, crack 156, and the back surface, respectively, would represent out-of-focus data—that is, data from out-of-focus impedance features (impedance features which were not within the depth of focus of the transducer 134).

Taking another example, in A-scan 158 reflectance data from occlusion 140 (reflectance 162) represents out-of-focus data, as the transducer 134 was focused on interface 144 when A-scan 158 was developed. However, in contrast with A-scan 148, in A-scan 158 interface 144 is within the depth of field of the transducer 134 and reflection 164 from interface 144 is in focus. Or stated another way, the interface 144 is an in-focus impedance feature in A-scan 158.

As noted, there are applications where it will be of value to create an image of a feature by gating the A-scan at an out-of-focus impedance feature. For example, in a sample which has a well-bonded silicon-to-silicon interface, the imaging of an absorptive or scattering feature at the interface will be difficult because of the close impedance match at the interface. A completely well-bonded sample interface gives a null result. A technique called "loss of back echo" is commonly used in this situation. This technique focuses the ultrasonic probe approximately at the interface of interest, and gates at the back surface of the sample. By scanning along the interface and observing (gating) for a loss of echo from the back surface, an in-focus image of such a feature can be created.

Each of the A-scans 148, 158, 166 exhibits many small undulations which contain valuable information about the impedance features within the sample. By the present invention, not only are the major echoes captured, but all information in the A-scan at each interrogated point throughout the volume of the sample are also stored. Using a sampling rate of 1 GHz, for example and an A-scan capture gate of 4 microseconds, 4000 data samples will be captured and stored in memory.

The amount of data that will be stored is the product of the scanning resolution in the X, Y plane, the number of planes scanned along the Z axes, and the number of data samples developed per A-scan (4000 in the present example). By way of example, the X-Y scanning resolution might be set at 256. times. 240, 10 planes may be scanned in the direction, and 4000 data samples may be stored per A-scan.

In accordance with an aspect of the present method, as alluded to above the captured A-scan data are amplified before digitization and storage. The amplification is adjusted to compensate the stored data (and ultimately data displays) for acoustic reflectance signal amplitude errors. One source of significant signal amplitude errors which may be compensated for is attenuation of acoustic energy by the sample.

All samples attenuate acoustic energy, and as is well known, some materials such as IC epoxy encapsulant are very highly absorptive of acoustic energy, with the result that reflections from impedance features at the bottom of the sample will appear weakly reflected simply because the two-way transmission of the acoustic waves to and from such a feature will result in dramatically more attenuation than from a feature near the surface.

Unlike the described prior method which makes a single scan in the X-Y plane and stores the A-scans of each x,y point in that plane, in the method of the present invention the multiple acoustic reflectance signals for each x,y plane interrogated may be retrieved and individually viewed. Or they may be retrieved and processed together to develop new acoustic reflectance information not otherwise obtainable. Processing together signals representing data characterizing reflections from "out-of-focus" impedance features and "in-focus" features is apt to produce valuable new insights as to the nature of the examined features.

In accordance with an extension of the method just described, signal segments from different A-scans are "stitched together" to produce a composite signal, all parts of which represent acoustic reflections from in-focus impedance features. This represents an especially useful subset of the complete 4D virtual sample wherein all out-of-focus data are eliminated from the 4D data. This in-focus subset of the 4D data can be obtained from an existing complete 4D dataset, or it can be obtained at the time of sample interrogation and data capture, minimizing data throughput and storage requirements.

In more detail, that method of capturing the complete data and then minimizing the dataset may be understood as having use in a scanning acoustic microscope having a pulsed ultrasonic probe on a Z axis and a probe translation stage for translating the probe in an X-Y plane of a sample. The method is directed to capturing space-time virtual sample data characterizing acoustic impedance features in multiple scans of a sample interrogated with the pulsed ultrasonic probe and producing a 4D virtual sample dataset of predetermined acoustic reflectance fidelity. The method comprises:

a. determining the desired level of acoustic reflectance fidelity by dividing the thickness of the sample Z-depth to be examined by the desired depth resolution to derive a quotient "q";

b. selecting a probe having a depth of field no greater than the desired depth resolution;

c. scanning the probe in the X-Y plane along first series of inspection points;

d. sensing and storing a digitized, non-peak-detected, time-varying acoustic reflectance signal for each interrogated point in the X-Y plane;

e. repeating the X-Y plane scanning, sensing, and storing operations for successive "z" values to a total of "q" times;

f. adjusting the location of the depth of field of the probe during each such operation such that successive portions of the sample are within the probe depth of focus when the acoustic reflectance signals are stored;

g. for each of specific values of "x,y" in the X-Y plane, retrieving the stored acoustic reflectance signals for "q" different values of "z", and eliminating the stored acoustic reflectance signals that do not correspond to Z-depths in the sample substantially equal to the depth of field of the probe;

h. for each such specific values of "x,y", effectively joining in-focus acoustic reflectance signal segments from adjacent "z" values in the sample to produce a synthesized optimally scanned A-scan, all parts of which represent in-focus acoustic reflectance data;

i. retrieving the stored synthesized composite acoustic reflectance signals for at least selected values of "x,y,z" in the examined sample; and j. employing the synthesized composite signals to modulate a display exhibiting only acoustic reflectance data from in-focus impedance features.

For the optimally scanned case (not overscanned or underscanned in "Z"), there is one and only one in-focus A-scan value at each sample time between the start and end of the capture gate. This in-focus sequence of A-scan values creates a synthesized A-scan that is effectively optimally focused at all points. As discussed elsewhere herein, if the amplitude was adjusted as a function of "Z" during the scanning operations, the A-scan data can also be caused to have consistent amplitude.

Figures 21, 22, 23:
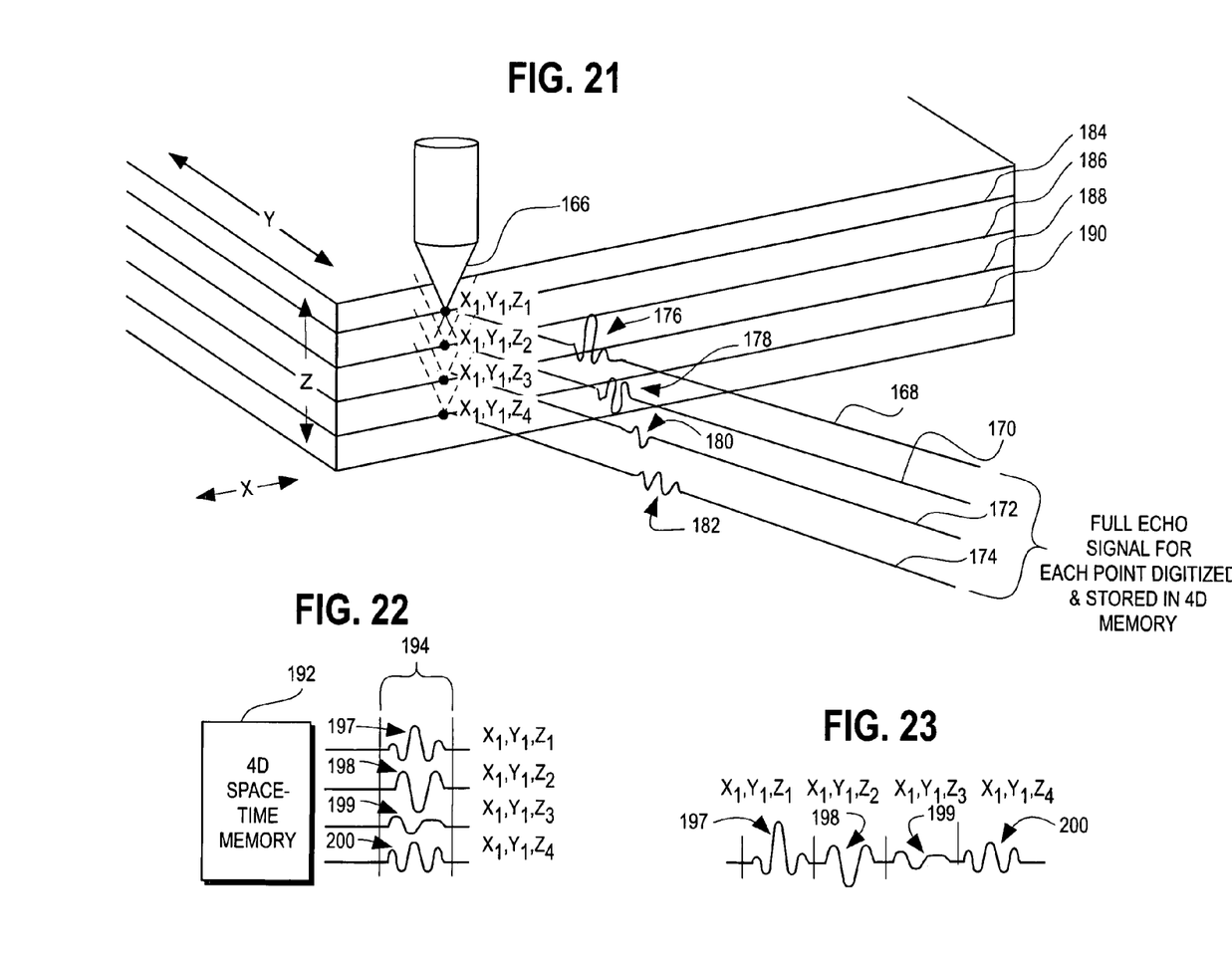

FIGS. 21, 22 and 23 will be helpful in understanding how the described composite signal is generated. FIG. 21 shows a transducer probe 166 positioned successively at points (x1,y1,z1), (x1,y1,z2), (x1,y1,z3), and (x1,y1,z4), developing A-scans 168, 170, 172, and 174. (For convenience only the reflections 176, 178, 180, 182 from interfaces 184, 186, 188, 190 are shown, although the entire waveform is digitized and captured in 4D space-time memory 192. A-scans 168, 170,172 and 174 are retrieved from the memory 192. A gate 194 is set in width and time location to capture just the in-focus reflections 176, 178, 180, 182 from interfaces 184, 186, 188, 190. The resulting gated signal segments 197, 198, 199, and 200 are then electronically "stitched" (joined) together to form a composite waveform 196. As described, composite waveform represents only acoustic reflectance data from in-focus impedance features, in this case interfaces 184, 186, 188, and 190.

When composite acoustic reflectance signals thus formed are employed to modulate a display of examined volume data, for any displayed slice at any set value of "x, "y", or "z", all parts of the display will exhibit acoustic reflectance information from in-focus impedance features.

The complete 4D space-time dataset captured by the method and apparatus of the present invention represents a virtual sample for the given transducer. Any type of image that is desired can be generated from this data. All of the resulting images will be uniformly in focus and of optimum brightness. All possible data for the sample for a given transducer will have been captured.

For attenuating samples, the ability to adjust for image brightness for each of many Z positions is valuable. Even when the entire thickness of a sample is within the focal region of the transducer, the brightness of a shallow feature may be significantly higher than the brightness of a deep defect if the gain is not adjusted. Even amounts of attenuation that are greater than the dynamic range of the waveform digitizer can be compensated for.

In accordance with the present invention, compared to prior methods, reflectance features are captured with dramatically greater detail. In the present example, the 10 A-scans will be very different in amplitude configuration. The amplitude value characterizing a particular impedance feature will vary significantly among the 10 A-scans depending principally upon the location of the transducer focal point relative to the location of the particular impedance feature.

For example, if the transducer is positioned in the X-Y plane at x10y30 and excited 10 times at different values of "z" throughout the depth of a sample, 10 A-scans will be developed. A detectable impedance feature located at x10y30z5 will appear in each A-scan, but at different amplitudes, depending, as stated, upon the location of the interrogating probe relative to x10y30z5.

In certain A-scans the particular impedance feature will be in focus, as defined herein, and in others it will be out of focus. In accordance with one execution of the present invention all 4000 sampled values for each of the 10 (in this example) A-scans will be stored.

In preferred executions of the invention, the four axes in the 4D data are:

1) X position of transducer (encoder counts)—measured in scanner space;

2) Y position of transducer (encoder counts)—measured in scanner space;

3) Z position of transducer—measured by TOF value (.mu. sec); and

4) Time axis of A-scan—time between points governed by sampling rate (nsec or. mu. sec)

The following examples will assist in an understanding of the invention. Assume ten scans at different values of the Z position of the transducer (slices). Assume an image resolution of 256 (X) and 240 (Y). Further assume that the 'capture gate' always starts before the top surface of the sample and the duration of the 'capture gate' is long enough to include a little more than the entire thickness of the sample. Finally, assume that there are 4000 points in each A-scan.

EXAMPLE 1

For one unique set of points in 4-space, which correlates to a unique position of the transducer (X1, Y1, Z1), there will be the 4000 values, one for each of the A-scan points captured at that position. If the capture gate is set as indicated for this sample, then there will be A-scan values that are equally spaced in time and that start before the top surface of the sample and that end after the bottom surface of the sample.

EXAMPLE 2

For another unique set of points in 4-space (X3, Y4, and T='150 samples later than the sample point that correlates to the sample surface',) there will be 10 different values, one for each of the 10 different Z positions of the transducer used for the ten different slices.

EXAMPLE 3

For a third unique set of points in 4-space (Y19, Z6, and T='112 samples later than the sample point that correlates to the sample surface',) there will be 256 different values, one for each of the 256 different X positions of the transducer at which data were captured.

The resulting virtual sample will thus be captured in a full 4D data set which can be processed and displayed as though the live sample were present. Having the virtual sample may in some respects be an advantage over operations in real time, as processing speeds need not be so rapid when analyzing a virtual sample off line.

Whereas the FIGS. 20–23 method is described in the context of successive X-Y raster scans along the Z axis, in a more general sense the invention concerns taking a succession of scans with a probe at three-dimensionally varied locations in a sample or sample portion as the probe is moved in the direction of the probe axis. The location of the depth of field of the probe is adjusted during each scanning operation such that successive portions of the sample are within the probe depth of focus when the acoustic reflectance signals are stored.

Rather than storing the successively derived A-scans and later eliminating the stored signals that do not correspond to depths in the sample substantially equal to the depth of field of the probe, the undesired signals may be eliminated before signal storage.

The composite signals may be amplified before being stored, for example to compensate for known variances in signal amplitude. One such known variance is due to attenuation of acoustic energy by the sample.

The process of "stitching together" the signal segments may result in the creation of discontinuities at the junction or transition points between signal segments. In accordance with an aspect of this invention, such discontinuities may be suppressed by low-pass filtering, high-pass filtering, or by some combination of low-pass and high-pass filtering.

While particular executions of the present invention have been shown and described, it will be obvious to those skilled in the art that other changes and modifications may be made without departing from the invention in its broader aspects. The appended claims are intended to cover all such changes and modifications that fall within the true spirit and scope of the invention. The matter set forth in the foregoing description and accompanying drawings is offered by way of illustration only and not as a limitation on the scope of the invention.

What is claimed is:

1. A method for use in micro-imaging, said method comprising the steps of:
    emitting a pulse of acoustic energy from a transducer toward each one of a plurality of three-dimensionally varied points located within a given volume that is defined inside of a sample;
    causing said transducer to have, for each one of said pulses, a focal point that is disposed at the same location within the given volume of the sample as the corresponding one of the three dimensionally varied points;
    using said transducer to receive at least a portion of a reflection signal that corresponds to each one of said emitted pulses; and
    storing in a data memory at least a portion of said reflections signals,
    wherein each one of said reflection signals comprises an A-Scan of the sample that is in-focus at the point within the given volume of the sample corresponding thereto.

2. The method of claim 1, wherein the sample is a microelectronic sample.

3. The method of claim 1, wherein said three-dimensionally varied points represent a series of points in two or more X-Y planes displaced along a Z-axis of said transducer.

4. The method of claim 1, wherein one or more of said reflection signals stored in said data memory contain both peak reflectance data and at least some off-peak reflectance data.

5. The method of claim 4, wherein one or more of said reflection signals stored in said data memory contain substantially all detectable portions of reflectance data.

6. The method of claim 1, further comprising the step of retrieving selected ones of said reflection signals stored in said data memory, and creating therefrom a composite digitized signal which represents an in-focus image of any impedance features at a point in the given volume of the sample that corresponds to each selected one of said reflectance signals.

7. The method of claim 1, further comprising the step of allowing only a desired portion of one or more of said reflectance signals to be stored in said data memory.

8. The method of claim 7, further comprising the step of combining two or more of said reflection signals into an in-focus image at any location of interest within the sample.

9. The method of claim 1, further comprising the step of causing an in-focus representation of an impedance feature for an area of interest within the sample to be displayed on a display.

* * * * *